United States Patent [19]

Jones et al.

[11] Patent Number: 4,919,889
[45] Date of Patent: Apr. 24, 1990

[54] SAMPLE COLLECTION AND TRANSPORT FLUID COMPOSITION

[75] Inventors: Lynn A. Jones, Mountain View; Lloyd H. Smith, Davis; Nelson N. H. Teng, Hillsborough, all of Calif.

[73] Assignee: Aspen Diagnostics Corporation, Sunnyvale, Calif.

[21] Appl. No.: 244,984

[22] Filed: Sep. 15, 1988

[51] Int. Cl.⁵ .................... B01J 11/18; G01N 1/00; A01N 1/02
[52] U.S. Cl. .......................... 422/40; 435/1; 436/18; 436/65; 436/176; 436/826; 530/850
[58] Field of Search ............... 435/1; 422/40; 436/18, 436/65, 176, 826; 530/850

[56] References Cited

U.S. PATENT DOCUMENTS 3,682,776  8/1972  Grundmann et al. ................. 435/1
4,681,839  7/1987  Swartz .................................. 435/284

Primary Examiner—Robert A. Wax
Attorney, Agent, or Firm—William B. Walker

[57] ABSTRACT

Sensitive proteins in human biological secretion samples are preserved by dispersing them in an aqueous solution containing from 0.05 to 0.5M of a buffer which is effective to maintain the solution pH within the range of from 6.5 to 8.0; from 0.1 to 10 wt. % of a non-immune animal protein selected from the group consisting of albumin, ovalbumin, casein, glycoprotein and mixtures thereof; from 40 to 2000 kallikrein units/mL of an enzyme inhibitor of trypsin, chymotrypsin, kallikrein or plasmin; and from 0.01 to 0.1 wt. % of a bacteriostatic agent. The solution preferably also contains from 5 $\mu$M to 1 mM of a protease inhibitor; and from 1 to 10 mM of a chelating agent. Optimally, the enzyme inhibitor is aprotinin, the protease inhibitor is phenylmethylsulfonylfluoride, the non-immune animal protein is bovine serum albumin, and the protease inhibitor is phenylmethylsulfonylfluoride. 0.0 to 0.15 mM of a water-soluble non-interfering salt, such as NaCl, may be desired.

16 Claims, No Drawings

SAMPLE COLLECTION AND TRANSPORT FLUID COMPOSITION

FIELD OF THE INVENTION

This invention relates to an aqueous composition useful for preserving sensitive proteins in human secretion samples containing a component which is to be identified and/or measured. In particular, this invention relates to an aqueous composition which can preserve protein components such as fetal fibronectin in vaginal or cervical samples during storage and transport.

BACKGROUND OF THE INVENTION

Determination of the presence of certain fetal restricted antigens in vaginal and cervical samples has proved useful for verifying pregnancy, detecting ectopic pregnancy, detecting increased risk of preterm labor, or detecting rupture of the amniotic membrane. These methods are the subject of commonly assigned copending applications, Ser. Nos. 121,895, 121,900, 121,893 and 121,899, all filed Nov. 17, 1987 and commonly assigned application U.S. Ser. No. 244969 filed concurrently herewith, the disclosures of all of these applications being hereby incorporated by reference.

In these methods a sample is removed from an area within the vaginal cavity, such as the posterior fornix, cervical canal or uterine cavity, and the sample is examined to determine the presence or quantity of a fetal restricted antigen component, usually a protein such as fetal fibronectin, in the sample. The sample is removed with a swab, aspirator, suction device, lavage or the like and transferred to a suitable container for storage and transport to the testing laboratory. We have discovered that sensitive proteins such as fetal fibronectin are unstable in the sampled composition, and the protein analyte level declines during storage and transport, limiting the sensitivity of the testing methods.

OBJECTS AND SUMMARY OF THE INVENTION

It is an object of this invention to provide a liquid medium in which human secretion samples can be placed for storage and transport, and which preserves sensitive protein analytes such as fetal fibronectin.

It is a further object of this invention to provide a storage and transport medium in which the level of sensitive protein analytes is preserved, thereby increasing the accuracy and reliability of diagnostic decisions based on the detection and quantification of such analytes.

It is a still further object of this invention to provide a storage and transport medium which prevents proteolytic degradation of proteins contained in human biological secretions, prevents growth of deleterious microorganisms, provides a pH in which proteins are neither oxidized nor reduced, and which inhibits non-specific loss of analyte protein due to adsorption of the protein to walls of sample vials or other contact surfaces.

In the method of this invention, sensitive proteins in human biological secretion samples are preserved by dispersing them in the novel preservative solution of this invention. The solution is an aqueous solution comprising from 0.05 to 0.5 M of a buffer which is effective to maintain the solution pH within the range of from 6.5 to 8.0; from 0.1 to 10 wt. % of a non-immune animal protein selected from the group consisting of albumin, ovalbumin, casein, glycoprotein and mixtures thereof; from 40 to 2000 kallikrein units/mL of an enzyme inhibitor of trypsin, chymotrypsin, kallikrein and plasmin; from 5 $\mu$M to 1 mM of phenylmethylsulfonylfluoride (PMSF), a serine esterase inhibitor; and from 0.01 to 0.1 wt. % of a bacteriostatic agent. The preservative solution also preferably contains from 5 $\mu$M to 1 mM of a protease inhibitor; from 1 to 10 mM of a chelating agent; and from 0.0 to 0.15 M of a non-interfering water-soluble salt, preferably NaCl.

A preferred solution contains from 0.05 to 0.5 M of a buffer which is effective to maintain the solution pH within the range of from 6.5 to 8.0; from 0.1 to 10 wt. % of an animal albumin; from 40 to 2000 kallikrein units/mL of aprotinin; from 0.01 to 0.1 wt. % of sodium azide or thimerosal; from 5 $\mu$M to 1 mM of a phenylmethylsulfonylfluoride; and from 1 to 10 mM of a chelating agent. An optimum solution contains Tris-HCl buffer having a pH of about 7.4; about 1 wt. % bovine serum albumin; about 500 kallikrein units/mL of aprotinin; about 0.02 wt. % sodium azide; about 1 mM phenylmethylsulfonylfluoride; about 5 mM of EDTA; and from 0.0 to 0.15 M of a non-interfering water-soluble salt, preferably NaCl.

The method of this invention for preserving sensitive proteins in human biological secretion samples comprises dispersing the sample in the aqueous solutions described above.

DETAILED DESCRIPTION OF THE INVENTION

The composition of this invention is suitable for preserving sensitive proteins in body secretions such as the liquids found in the vaginal cavity including the posterior fornix, cervical canal and uterine cavity. It is particularly suitable for preserving fetal fibronectin and other fetal restricted proteins which are found in these secretions during early stages of pregnancy; in the later stages of pregnancy when risks of preterm labor increases; or when the amniotic membrane is ruptured. The human secretions which can be stabilized and preserved in the composition of this invention can be any body secretion, including but not limited to human secretions and tissues such as blood, plasma, serum, mucus, vaginal secretions, oral secretions, nasal secretions, anal secretions and the like. This invention is described hereinafter with respect to secretions obtained from the vaginal cavity including the posterior fornix and cervical canal for purposes of clarity and not by way of limitation. It is a critical feature of this composition that it does not introduce substances which will adversely affect or interfere with immunoassay qualification or quantification of analytes in the sample.

The composition of this invention is an aqueous buffered solution containing a quantity of a suitable buffer to maintain a solution pH within the range of from 6.5 to 8.0. Suitable buffers include Tris-HCl buffers having the pH adjusted to within the desired range, preferably in a 0.05 to 0.5 M concentration. Alternate buffers include sodium phosphate buffer, citrate phosphate buffer, Hepes buffer, and the like having the pH adjusted to within the desired range, preferably in a 0.05 to 0.5 M concentration. A 0.05 M Tris-HCl solution having a pH adjusted to about 7.4 is optimum.

The composition is preferably adjusted to a physiological isotonic state with a non-interfering water-soluble salt. An optimum non-interfering salt is sodium chloride. The preferred composition aids in preventing hypotonic or hypertonic rupture of cells, which causes a release of proteolytic enzymes and interfering substances.

The composition also contains from 0.1 to 10 wt. % of a non-immune animal protein. This component reduces adsorption of analyte protein on the surfaces of vials and other articles with which the sample is contacted and stabilizes the protein analyte. Suitable water-soluble non-immune animal proteins include albumins such as bovine, human, rabbit, goat, sheep, and horse serum albumins; and other animal proteins such as casein, ovalbumin, glycoproteins, and the like. Bovine serum albumin from 1 to 5 wt. % is preferred.

The composition contains from 40 to 2000 kallikrein units/mL of an inhibitor of proteolytic enzymes commonly found in human bodily secretions. Example of such proteolytic enzymes are trypsin, chymotrypsin, kallikrein and plasmin. Suitable proteolytic enzyme inhibitors include aprotinin, a preferred inhibitor; 6-amino-n-hexanoic acid, a plasmin inhibitor; kallikrein inhibitor; soybean trypsin inhibitor; trypsin-chymotrypsin inhibitor (Bowman-Birk inhibitor); chymostatin; and the like. A preferred inhibitor concentration is about 500 kallikrein units/mL.

The composition contains a bacteriostatic agent for inhibiting microbial growth. Sodium azide and thimerosal are suitable bacteriostatic agents in concentrations of from 0.01 to 0.1 wt. %.

A bacteriostatic agent concentration of about 0.02 wt. % is preferred.

A preferred component is a protease inhibitor, which reacts with active sites of proteases, blocking proteolytic activity. An optimum protease inhibitor is PMSF (phenylmethylsulfonylfluoride) in concentrations of 5 $\mu$M to 1 mM.

Another preferred component of the composition is an amount of a chelating agent which is effective to complex divalent cations required in many proteolytic processes. Suitable chelating agents include EDTA, EGTA, DTPA, and the like. A comprehensive description of suitable chelating agents and methods for their manufacture is provided in U.S. Pat. No. 4,647,447, the entire contents of which are hereby incorporated by reference in their entirety. Chelating agent concentrations of from 1 to 10 mM and optimally about 5 mM (for EDTA) can be used.

This invention is further illustrated by the following specific, but non-limiting example. Temperatures are given in degrees Centigrade and percents as weight percents unless otherwise specified. Examples which are constructively reduced to practice herein are presented in the present tense, and examples representing laboratory experiments previously reduced to practice are presented in the past tense.

EXAMPLE 1

Amniotic fluid extracted from swabs was placed in 0.5 mL aliquots of the sample preservative solution of this invention in collection vials. The solution consisted of 0.05 M Tris-HCl, pH 7.4; 0.15 M NaCl, 0.02 wt. % NaN$_3$, wt. % BSA, 500 Kallikrein Units/mL of aprotinin, 1 mM phenylmethylsulfonylfluoride (PMSF) and 5 mM EDTA.

For comparison, amniotic fluid extracted from swabs obtained in the same manner were immersed in PBS-BSA (0.01 sodium phosphate buffer, pH 7.4, containing 0.15 M sodium chloride and 0.02 wt. % sodium azide and 1 wt. % bovine serum albumin).

A vial of each solution was stored at $-20°$ C., 4° C., and 22° C., and compared to time zero fetal fibronectin levels by the test procedure described below.

The positive control was amniotic fluid of known fetal fibronectin concentration, appropriately diluted to fall within the assay range (20 ng/mL to 5 $\mu$g/mL for a monoclonal based assay). The negative control was sample diluent. The Assay Standard was amniotic fluid of known fibronectin concentration, serially diluted in sample diluent to provide a standard curve, ranging from 20 ng to 5$\mu$g/mL.

A microtiter plate was prepared by the following procedure:

Goat F(ab')$_2$ anti-mouse IgG antibody (Tago) was diluted to 10 $\mu$g/mL in 0.05 M carbonate buffer, pH 9.6. 100 $\mu$L was dispensed into each well of an IMMULON II microtiter plate (Dynatech). The plate was covered and incubated 4 hr at room temperature or 4° C. overnight. The plate was washed 4 times with Wash Buffer and blocked. Mouse monoclonal anti-(fetal fibronectin) ascites prepared as described in concurrently filled application Ser. No. 244969 was diluted 1/5000 with 0.01 M PBS-1 wt. % BSA, pH 7.4. 100 $\mu$L of the solution was dispensed into each well of the blocked microtiter plate. The wells were covered and incubated for 2 hr at room temperature or overnight at 4° C. The plate was then washed 4 times with Wash Buffer as described above, and was then ready for immunoassay of samples.

100 $\mu$L of each of standard, sample, and positive and negative control were placed in separate wells and incubated 2 hr at room temperature. The plate was washed 4 times with Wash Buffer (0.02 M Tris HCl, 0.015 M NaCl, 0.05% TWEEN-20), filling and emptying the wells completely with each use. 100 $\mu$L of alkaline phosphatase-conjugated goat anti-(human fibronectin) antibody, prepared following the one-step glutaraldehyde procedure of Avrameas, *Immunochem.* 6:43 (1969), was diluted 1/1,000 in Conjugate Buffer (0.02 M Tris-HCl, pH 8, 0.03 M NaCl, 0.05 wt. % TWEEN 20, 5 wt. % BSA, 0.02 wt. % NaN$_3$). 100 $\mu$L was dispensed into each well and incubated for 2 hr at room temperature. The plate was washed 4 times as previously described. 4 mg/mL of p-nitrophenylphosphate (PNPP) was used as the substrate. This was diluted in 0.18 M 2-amino-2-methyl-1-propanol (AMP) buffer, pH 9.5, with 0.12 mM MgCl$_2$. 100 $\mu$L was dispensed into each well of the microtiter plate. After a 5 min incubation at room temperature, the reaction rate in milli-OD/min was read at 405 nm on a V-MAX ™ kinetic microtiter plate reader (Molecular Devices).

A standard curve was constructed by correlating increasing reaction rate with increasing fibronectin concentration in the standards. Unknowns were calculated directly from the curve or by using a preset computer program (Molecular Devices).

The samples were found to be stable in the composition of this invention for at least 6 months at $-20°$ C., 4° C. and 22° C. but were only stable for 10 days at the same temperatures in the PBS-BSA solution.

We claim:

1. An aqueous solution for preserving sensitive proteins in human biological secretion samples consisting essentially of
   (a) from 0.05 to 0.5 M of a buffer which is effective to maintain the solution pH within the range of from 6.5 to 8.0;

(b) from 0.1 to 10 wt. % of a non-immune animal protein selected from the group consisting of albumin, ovalbumin, casein, glycoprotein and mixtures thereof;

(c) from 40 to 2000 kallikrein units/mL of an enzyme inhibitor of trypsin, chymotrypsin, kallikrein or plasmin; and (d) from 0.01 to 0.1 wt. % of a bacteriostatic agent.

2. An aqueous solution of claim 1 wherein the enzyme inhibitor is aprotinin.

3. An aqueous solution of claim 1 including (e) from 5 μM to 1 mM of a protease inhibitor; and (f) from 1 to 10 mM of a chelating agent.

4. An aqueous solution of claim 3 wherein the protease inhibitor is phenylmethylsulfonylfluoride.

5. An aqueous solution of claim 3 wherein the enzyme inhibitor is aprotinin.

6. An aqueous solution of claim 3 wherein the chelating agent is EDTA.

7. An aqueous solution of claim 1 consisting essentially of (a) from 0.05 to 0.5 M of a buffer which is effective to maintain the solution pH within the range of from 6.5 to 8.0;

(b) from 0.1 to 10 wt. % of an animal albumin;

(c) from 40 to 2000 kallikrein units/mL of aprotinin;

(d) from 0.01 to 0.1 wt. % of sodium azide or thimerosal;

(e) from 5 μM to 1 mM of a phenylmethylsulfonylfluoride;

(f) from 1 to 10 mM of a chelating agent; and (g) from 0.0 to 0.15 mM of a non-interfering water-soluble salt.

8. An aqueous solution of claim 7 consisting essentially of (a) Tris-HCl buffer having a pH of 7.4;

(b) 1 wt. % bovine serum albumin;

(c) 500 kallikrein units/mL of aprotinin;

(d) 0.02 wt. % sodium azide;

(e) 1 mM phenylmethylsulfonylfluoride;

(f) 5 mM of EDTA; and (g) 0.15 mM NaCl.

9. A method for preserving sensitive proteins in human biological secretion samples comprising dispersing the sample in an aqueous solution consisting essentially of (a) from 0.05 to 0.5 M of a buffer which is effective to maintain the solution pH within the range of from 6.5 to 8.0;

(b) from 0.1 to 10 wt. % of a non-immune animal protein selected from the group consisting of albumin, ovalbumin, casein, glycoprotein and mixtures thereof;

(c) from 40 to 2000 kallikrein units/mL of an enzyme inhibitor of trypsin, chymotrypsin, kallikrein or plasmin; and (d) from 0.01 to 0.1 wt. % of a bacteriostatic agent.

10. A method of claim 9 wherein the enzyme inhibitor is aprotinin.

11. A method of claim 9 wherein the aqueous solution includes (e) from 5 μM to 1 mM of a protease inhibitor; and (f) from 1 to 10 mM of a chelating agent.

12. A method of claim 11 wherein the protease inhibitor is phenylmethylsulfonylfluoride.

13. A method of claim 11 wherein the enzyme inhibitor is aprotinin.

14. A method of claim 11 wherein the chelating agent is EDTA.

15. A method of claim 9 wherein the aqueous solution consists essentially of (a) from 0.05 to 0.5 M of a buffer which is effective to maintain the solution pH within the range of from 6.5 to 8.0;

(b) from 0.1 to 10 wt. % of an animal albumin;

(c) from 40 to 2000 kallikrein units/mL of aprotinin;

(d) from 0.01 to 0.1 wt. % of sodium azide or thimerosal;

(e) from 5 μM to 1 mM of a phenylmethylsulfonylfluoride;

(f) from 1 to 10 mM of a chelating agent; and (g) from 0.0 to 0.15 mM of a non-interfering water-soluble salt.

16. A method of claim 15 wherein the aqueous solution consists essentially of (a) Tris-HCl buffer having a pH of 7.4;

(b) 1 wt. % bovine serum albumin;

(c) 500 kallikrein units/mL of aprotinin;

(d) 0.02 wt. % sodium azide;

(e) 1 mM phenylmethylsulfonylfluoride;

(f) 5 mM of EDTA; and (g) 0.15 mM of NaCl.

* * * * *